United States Patent
Baldridge et al.

(10) Patent No.: US 11,845,719 B1
(45) Date of Patent: Dec. 19, 2023

(54) LIGHT ALKANES TO TRANSPORTATION FUEL

(71) Applicant: PHILLIPS 66 COMPANY, Houston, TX (US)

(72) Inventors: Anthony O. Baldridge, Bartlesville, OK (US); Matthew J. Wulfers, Owasso, OK (US); Neal D. McDaniel, Bartlesville, OK (US); Robert M. Walston, Skiatook, OK (US); Soumen Kundu, Pearland, TX (US); Bruce B Randolph, Sachse, TX (US)

(73) Assignee: Phillips 66 Company, Houston, TX (US)

( * ) Notice: Subject to any disclaimer, the term of this patent is extended or adjusted under 35 U.S.C. 154(b) by 0 days.

(21) Appl. No.: 18/314,591

(22) Filed: May 9, 2023

Related U.S. Application Data

(60) Provisional application No. 63/345,767, filed on May 25, 2022, provisional application No. 63/345,774, filed on May 25, 2022.

(51) Int. Cl.
  *C07C 6/10* (2006.01)
  *C07C 7/09* (2006.01)
  (Continued)

(52) U.S. Cl.
  CPC ............... *C07C 6/10* (2013.01); *B01D 3/14* (2013.01); *B01D 5/006* (2013.01); *B01J 8/0492* (2013.01); *C07C 7/09* (2013.01); *B01J 2208/00017* (2013.01); *B01J 2208/00539* (2013.01); *C07C 2529/40* (2013.01)

(58) Field of Classification Search
  CPC ......... C07C 6/10; C07C 7/09; C07C 2529/40; B01D 3/14; B01D 5/006; B01J 8/0492; B01J 2208/00017; B01J 2208/00539
  See application file for complete search history.

(56) References Cited

U.S. PATENT DOCUMENTS

| | | | | |
|---|---|---|---|---|
| 4,851,602 | A | * | 7/1989 | Harandi ................. C10G 50/00 585/323 |
| 2019/0300455 | A1 | * | 10/2019 | Baldridge ............ C10G 29/205 |

(Continued)

*Primary Examiner* — Ali Z Fadhel
(74) *Attorney, Agent, or Firm* — Phillips 66 Company

(57) ABSTRACT

The present disclosure relates generally to processes and systems for producing liquid transportation fuels by converting a feed stream that comprises both isopentane and n-pentane, and optionally, some C6+ hydrocarbons. Isopentane and smaller hydrocarbons are separated to form a first fraction while n-pentane and larger components of the feed stock form a second fraction. Each fraction is then catalytically-activated in a separate reaction zone with a separate catalyst, where the conditions maintained in each zone maximize the conversion of each fraction to olefins and aromatics, while minimizing the production of C1-C4 light paraffins. In certain embodiments, the first fraction is activated at a lower temperature than the second fraction. Certain embodiments additionally comprise mixing at least a portion of the two effluents and contacting with either an oligomerization catalyst or alkylation catalyst to provide enhanced yields of upgraded hydrocarbon products that are suitable for use as a blend component of liquid transportation fuels or other value-added chemical products.

20 Claims, 2 Drawing Sheets

(51) Int. Cl.
    *B01J 8/04*     (2006.01)
    *B01D 3/14*     (2006.01)
    *B01D 5/00*     (2006.01)

(56) References Cited

U.S. PATENT DOCUMENTS

| | | | |
|---|---|---|---|
| 2019/0300804 A1* | 10/2019 | Baldridge | C07C 4/06 |
| 2019/0300805 A1* | 10/2019 | Baldridge | C10G 45/64 |
| 2020/0109095 A1* | 4/2020 | Baldridge | C10G 63/02 |
| 2020/0109341 A1* | 4/2020 | Baldridge | C10G 69/123 |
| 2020/0339887 A1* | 10/2020 | Baldridge | C10G 65/043 |
| 2020/0339888 A1* | 10/2020 | Baldridge | C10G 65/043 |
| 2020/0339896 A1* | 10/2020 | Baldridge | C10G 45/64 |

* cited by examiner

LIGHT ALKANES TO TRANSPORTATION FUEL

CROSS-REFERENCE TO RELATED APPLICATIONS

This application is a non-provisional application which claims the benefit of and priority to U.S. Provisional Application Ser. No. 63/345,767 filed May 25, 2022, entitled "Light Alkanes to Transportation Fuel," and U.S. Provisional Application Ser. No. 63/345,774 filed May 25, 2022, entitled "Systems for Light Alkanes to Transportation Fuel" both of which are hereby incorporated by reference in its entirety.

STATEMENT REGARDING FEDERALLY SPONSORED RESEARCH OR DEVELOPMENT

None.

FIELD OF THE INVENTION

The present disclosure relates to processes and systems for catalytically upgrading a feed stream predominantly comprising light alkanes by a two-step activation to produce olefins and aromatics in an approximate 1:1 ratio that facilitates alkylation of the aromatics with the olefins to produce a liquid hydrocarbon transportation fuel blend stock.

BACKGROUND

A large surplus of pentanes are available in the petroleum refining industry, arising predominantly from the increased production of light hydrocarbons from U.S. shale formations, and also from regulatory limits on the quantity of volatile hydrocarbon components that can be blended into finished transportation fuels, which must adhere to regulations on minimum vapor pressure. Unfortunately, conventional processes for upgrading light alkanes to value-added products are not well-suited for hydrocarbon feed streams that primarily comprise pentanes (i.e., isopentane and n-pentane). Therefore, it would be beneficial to find improved processes and systems for efficiently converting pentanes to more valuable products, including transportation fuels and chemicals, while minimizing the production of C1-C4 light paraffins.

Much recent research has focused on the conversion of light alkanes (including butanes and pentanes) to aromatics by impregnating zeolites with metals. This has been shown to decrease side-reactions (e.g., protolytic cracking, hydride transfer, etc.) that limit selectivity to aromatics. However, the metal-impregnated zeolites utilized for such processes generally have a shorter catalytic lifespan when commercially implemented as the impregnated metals are more susceptible to inactivation by certain contaminants present in the feed stream, such as, but not limited to, compounds containing one or more of sulfur, nitrogen, arsenic and lead. What is needed are lower cost processes and systems that produce maximize production of monoalkylated aromatics from pentane (and/or isobutane) feeds while limiting production of C1-C4 olefins.

The inventive processes and systems disclosed herein provide an improved upgrading route for pentane-rich mixtures that may include, for example, fuel blend stocks and other pentane-rich streams that do not government specifications for use as a liquid transportation fuel blend stock. The inventive processes and systems provide enhanced yields of more valuable hydrocarbon upgraded products that meet government specifications for use as a transportation fuel component or as a feed stream for processes that produce other value-added chemical products.

BRIEF SUMMARY OF THE DISCLOSURE

Some embodiments comprise a method for converting a feed stream comprising pentanes to produce a liquid transportation fuel, comprising: a) providing a hydrocarbon feed stream comprising at least 50 wt. % pentanes and less than 10 wt. % hydrocarbons that contain four or fewer carbon atoms; b) contacting the hydrocarbon feed stream with a first catalyst comprising a zeolite at conditions comprising a first temperature and a first pressure that facilitate conversion of at least a portion of the first fraction by the first catalyst to produce a first effluent comprising olefins containing from two to five carbon atoms, monocyclic aromatics and alkanes containing from two to five carbon atoms; c) contacting the first effluent with a second catalyst at conditions comprising a second temperature and second pressure that facilitate conversion of the first effluent by the second catalyst to produce a second effluent comprising monocyclic aromatics and olefins containing from two to five carbon atoms at a molar ratio that is in the range from 0.75 to 1.25, wherein the second catalyst has a distinct chemical composition from the first catalyst; wherein the second temperature is at least 25° C. lower than the first temperature; d) contacting the second effluent with an alkylation catalyst at a third temperature and a third pressure that facilitate alkylation of at least a portion of the aromatics in the second effluent with at least a portion of the olefins present in the second effluent by the alkylation catalyst to produce an alkylation effluent comprising an increased quantity of mono-alkylated aromatics containing eight or nine carbon atoms relative to the quantity of mono-alkylated aromatics containing eight or nine carbon atoms in the second effluent, wherein the alkylation effluent comprises at least 50 wt. % monoalkylated aromatics containing from 7 to 9 carbon atoms; e) at least partially condensing the alkylation effluent to produce a heavy hydrocarbons fraction comprising hydrocarbons containing at least five carbon atoms and a light hydrocarbons fraction comprising hydrocarbons containing four or less carbon atoms; f) separating a C5 fraction comprising pentanes from the heavy hydrocarbon fraction to produce an aromatics product comprising mono-alkylated aromatics and residual benzene that meets specifications for a component of a liquid transportation fuel; g) redirecting the C5 fraction to be combined with the feed stream.

In some embodiments, the contacting of the first effluent with the second catalyst at conditions comprising a second temperature and second pressure facilitates conversion of the second fraction by the second catalyst to produce a second effluent comprising monocyclic aromatics and olefins containing from two to five carbon atoms at a molar ratio that is in the range from 0.9 to 1.1.

In some embodiments, the first catalyst and the second catalyst are zeolites that do not comprise metals other than aluminum.

In some embodiments, the hydrocarbon feed stream comprises less than 5 wt. % of hydrocarbons containing four or fewer carbon atoms. In some embodiments, the hydrocarbon feed stream comprises at least 60 wt. % pentanes.

In some embodiments, the first temperature is in the range from 500° C. to 650° C. and the first pressure is in the range from 0 psig to 150 psig. In some embodiments, the second temperature is in the range from 475° C. to 625° C. and the second pressure is in the range from 0 psig to 500 psig. In some embodiments, the third temperature is in the range from 150° C. to 350 °C. and the third pressure is in the range from 35 psig to 600 psig.

In some embodiments, the second temperature is at least 25° C. lower than first temperature. In some embodiments, the second temperature is at least 50° C. lower than first temperature. In some embodiments, the second pressure is at least 50 psi (3.45 Bar) higher than the first pressure.

In some embodiments, the hydrocarbon feed stream comprises at least 70 wt. % pentanes and less than 10 wt. % hydrocarbons containing either from one to four carbon atoms or at least seven carbon atoms. In some embodiments, the hydrocarbon feed stream comprises at least 70 wt. % isobutane and less than 10 wt. % of n-butane or other hydrocarbons containing either from one to four carbon atoms or at least seven carbon atoms.

In some embodiments, the method further comprises adding a hydrocarbon diluent to the feed stream prior to the contacting of b) wherein the diluent is inert at the conditions of temperature and pressure that are maintained in the first catalyst bed. In some embodiments, the hydrocarbon diluent comprises light alkanes containing from one to four carbon atoms. In some embodiments, the diluent is selected from methane, ethane, propane, butane and combinations thereof. In some embodiments, the diluent is obtained by separating C1-C4 hydrocarbons from the light fraction and redirecting the C1-C4 alkanes to be combined with the feed stream as the diluent.

Some embodiments comprise a system for converting a feed stream comprising pentanes to produce a liquid transportation fuel or a component thereof, comprising: a) a first reactor comprising a first catalyst bed that contains a first catalyst comprising a zeolite, wherein the first reactor is operable to receive a hydrocarbon feed stream a hydrocarbon feed stream comprising at least 50 wt. % pentanes and less than 10 wt. % hydrocarbons that contain either from one to four or at least seven carbon atoms and to facilitate contact between the hydrocarbon feed stream and the first catalyst, wherein the first reactor is further operable to maintain the first catalyst bed at a first temperature and a first pressure that facilitates the catalytic conversion of the hydrocarbon feed stream by the first catalyst to produce a first effluent comprising olefins containing from two to five carbon atoms, monocyclic aromatics and unconverted alkanes containing from two to five carbon atoms; b) a second reactor comprising a second catalyst bed that contains a second catalyst comprising a zeolite, wherein the second reactor is operable to receive the first effluent and to facilitate contact between the first effluent and the second catalyst, wherein the second reactor is further operable to maintain the second catalyst bed at a second temperature that is at least 25° C. lower than the first temperature and a pressure that is at least 50 psig (3.45 Bar) higher than the first pressure to facilitate the catalytic conversion of the first effluent by the second catalyst to produce a second effluent comprising monocyclic aromatics and olefins containing from two to five carbon atoms at a molar ratio that is in the range from 0.75 to 1.25, wherein the second catalyst has a distinct chemical composition from the first catalyst; wherein the second temperature is at least 25° C. lower than the first temperature; c) a third reactor comprising a third reaction zone that contains an alkylation catalyst, wherein the third reactor is operable to receive the second effluent and facilitate contact between the second effluent and the alkylation catalyst in the third reaction zone, wherein the third reactor is operable to maintain the third reaction zone at a temperature and a pressure that facilitates alkylation of the monocyclic aromatics in the second effluent with the C2-C4 olefins from second effluent to produce an alkylation effluent comprising an increased quantity of mono-alkylated aromatics containing eight or nine carbon atoms relative to the quantity of mono-alkylated aromatics containing eight or nine carbon atoms in the second effluent; d) a first separator operable to separate and partially condense the alkylation effluent to produce a heavy fraction and a light fraction, wherein the heavy fraction comprises monocyclic aromatics and unreacted alkanes containing at least five carbon atoms, wherein the light fraction comprises hydrogen and at least 80 wt. % olefins and alkanes containing four or fewer carbon atoms; d) a second separator operable to separate a benzene stream from the heavy fraction to produce an aromatics product comprising mono-alkylated aromatics and residual benzene that meets specifications for a component of a liquid transportation fuel, wherien the system further comprises a first conduit operable to convey the benzene stream to be combined with the second effluent; e) a third separator operable to separate hydrogen from the light fraction to produce a diluent stream comprising C1-C4 olefins and alkanes, wherein the system further comprises a second conduit operable to convey the recycle stream to be combined with the feed stream.

Some embodiments of the system further comprise a compressor operable to compress the second effluent to produce a compressed second effluent that is at a higher pressure than the second effluent, wherein the alkylation reactor is operable to receive the compressed second effluent.

In some embodiments of the system, the alkylation reactor is operable to receive a benzene stream in addition to the heavy hydrocarbons fraction and a first portion of the light hydrocarbons fraction. In some embodiments of the system, the benzene stream is recycled from the second separator.

In some embodiments of the system, the first reactor is operable to maintain a first temperature in the first catalyst bed that is in the range from 500° C. to 650° C. and a pressure in the first catalyst bed that is in the range from 15 psig to 150 psig. In some embodiments of the system, the second reactor is operable to maintain the second temperature in the range from 475° C. to 625° C. and the second pressure in the range from 0 psig to 500 psig. In some embodiments of the system, the third reactor is operable to maintain the third temperature in the range from 150° C. to 350° C. and the third pressure in the range from 35 psig to 600 psig.

In some embodiments of the system, the second reactor is operable to maintain the second catalyst bed at a temperature that is at least 25° C. lower than first temperature. In some embodiments of the system, the second reactor is operable to maintain the second catalyst bed at a temperature that is at least 50° C. lower than first temperature. In some embodiments of the system, the second reactor is operable to maintain the second pressure at a value that is at least 50 psi (3.45 Bar) higher than the first pressure.

BRIEF DESCRIPTION OF THE DRAWINGS

A more complete understanding of the present invention and benefits thereof may be acquired by referring to the follow description taken in conjunction with the accompanying drawings in which.

Figure 1:
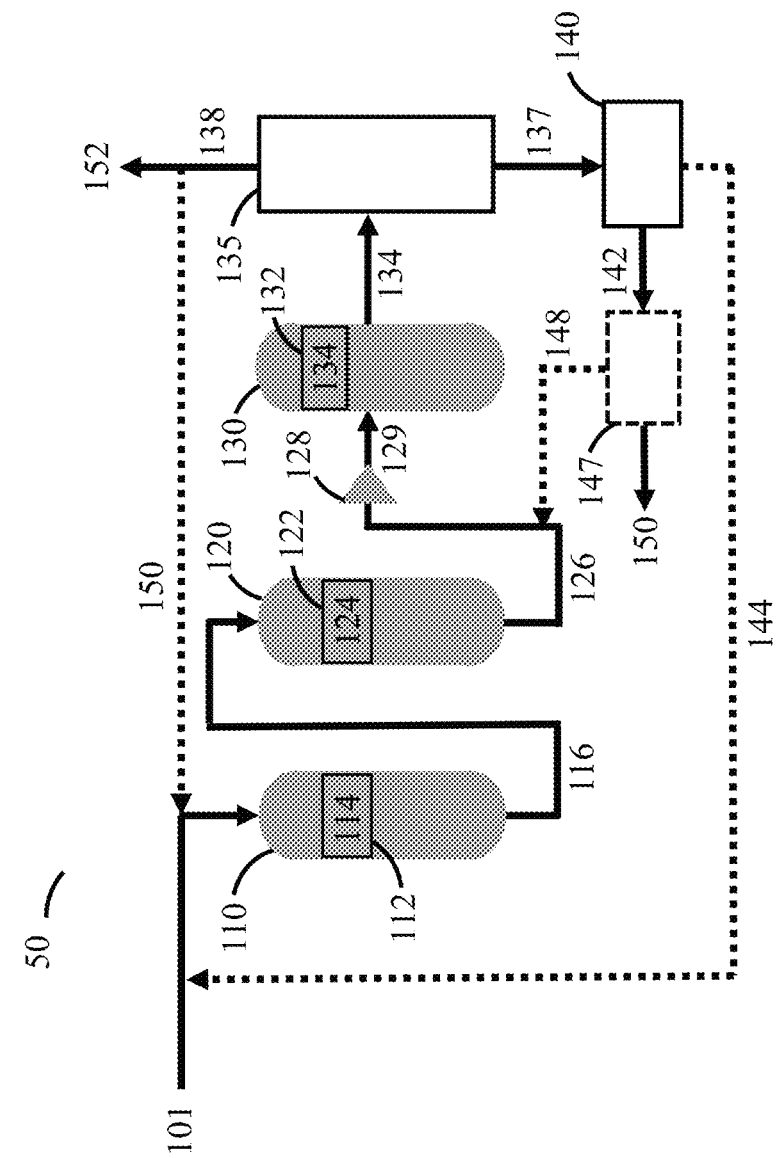
FIG. 1 is a flow diagram depicting a first embodiment of the inventive processes and systems.

The invention is susceptible to various modifications and alternative forms, specific embodiments thereof are shown by way of example in the drawings. The drawings may not be to scale. It should be understood that the drawings are not intended to limit the scope of the invention to the particular embodiment illustrated.

DETAILED DESCRIPTION

The present disclosure provides processes to convert a mixture of light hydrocarbons to liquid transportation fuels. The process and systems described herein relate primarily to the conversion of a feed stream comprising light hydrocarbon containing in the range from two to nine carbons, or any subset thereof. In some embodiments, the feed stream predominantly comprises pentanes to generate upgraded products that meet specifications for a blend component of a liquid transportation fuel.

The feed stream is catalytically activated in a two-step activation that occurs in two separate catalyst beds arranged in series. The feed stream is received in a first catalyst bed and catalytically activated in the first catalyst bed by contacting a first catalyst to produce a first effluent comprising olefins and aromatics. The entire first effluent is then immediately conveyed to a second catalyst bed that contained within a second reactor and maintained at a temperature that is approximately 50 degrees cooler than the first catalyst bed (measured at the start or inlet of the catalyst bed). The first effluent is catalytically activated in the second catalyst bed by contacting a second catalyst that is compositionally distinct from the first catalyst to produce a second effluent that comprises aromatics and olefins in an approximate 1:1 molar ratio. The second effluent is then further upgraded by in a third reaction zone by oligomerization and/or alkylation to produce value-added chemicals and/or products including larger hydrocarbons and alkylated aromatics that meet specifications as a liquid transportation fuel blend component. An advantage of the inventive processes and systems is a significant decrease in production of light alkanes containing from 1-4 carbon atoms that do not meet government specifications for use as a transportation fuel and are typically referred to as fuel gas. Additional advantages will become evident from the detailed disclosure provided below.

In some embodiments, the feed stream is generally comprised of light alkanes and is enriched in pentanes (C5), although feed streams suitable for use with the inventive processes and systems may additionally comprise alkanes containing from one to four carbons or from six to nine carbons. In certain embodiments, the feed stream comprises at least 20 wt. % pentanes; optionally, at least 30 wt. % pentanes; optionally, at least 40 wt. % pentanes; optionally, at least 50 wt. % pentanes; %; optionally, at least 60 wt. % pentanes; %; optionally, at least 70 wt. % pentanes; optionally, at least 80 wt. % pentanes; optionally, at least 90 wt. % pentanes.

In some embodiments, the feed stream is generally comprised of light alkanes and is enriched in butanes (C4), although feed streams suitable for use with the inventive processes and systems may additionally comprise alkanes containing from one to three carbons or from five to nine carbons. In certain embodiments, the feed stream comprises at least 20 wt. % butanes; optionally, at least 30 wt. % butanes; optionally, at least 40 wt. % butanes; optionally, at least 50 wt. % butanes; %; optionally, at least 60 wt. % butanes; %; optionally, at least 70 wt. % butanes; optionally, at least 80 wt. % butanes; optionally, at least 90 wt. % butanes.

In certain embodiments, the feed stream may be obtained by processing a stream of natural gas liquids to remove lighter hydrocarbon components (i.e., C1-C4) by way of conventional natural gas separation technologies that are well-characterized, such as, for example, de-methanizer, de-ethanizer, de-propanizer and de-butanizer fractionation columns. A typical product of such separation technologies is commonly characterized as natural gasoline, comprising about 72 wt. % pentanes, with a majority of the remainder comprising C6 hydrocarbons.

A first embodiment of the inventive processes and systems is illustrated by the process flow-diagram of FIG. 1. A feed stream 101 that is enriched in pentanes is converted in a system 50. The feed stream 101 is received by a first reactor 110 comprising a first catalyst bed 112 that contains a first catalyst 114. The first reactor 110 is operable to receive the feed stream 101 and to maintain a temperature and a pressure in the first catalyst bed 112 that facilitates catalytic conversion of the feed stream 101 by the first catalyst 114 to produce a first effluent 116 comprising predominantly C2-C5 olefins, along with some monocyclic aromatics and alkanes (including unreacted pentanes).

The first effluent 116 is conveyed to and received by a second reactor 120 that comprises a second catalyst bed 122 containing a second catalyst 124. The second reactor 120 is operable to receive maintain a temperature and a pressure in the second catalyst bed 122 that facilitates conversion of the first effluent 116 by the second catalyst 124 to produce a second effluent 126 that is enriched in monocyclic aromatic content (on a molar basis relative to the first effluent) and additionally comprises olefins and some residual alkanes, including unreacted pentanes from the feed stream.

The second effluent 126 is next conveyed to a compressor 128 that compresses the second effluent to a pressure that is higher than the pressure that is maintained in the first reactor 110 and second reactor 120 to produce a compressed second effluent 129 that is immediately conveyed to alkylation reactor 130 that comprises an alkylation catalyst bed 132 containing an alkylation catalyst 134. The alkylation reactor 130 is designed to maintain a temperature and a pressure that facilitates the contacting of the compressed second effluent 129 with the alkylation catalyst 134 at a temperature and a pressure that facilitate the alkylation of monocyclic aromatics in the compressed second effluent 129 with C1-C4 olefins present in the compressed second effluent to produce an alkylation effluent 134 that is enriched in mono-alkylated aromatics.

The alkylation effluent 134 is conveyed to and received by first separator 135, which is designed to separate hydrocarbons according to boiling point and thereby produce a light fraction 138 comprising C1-C4 hydrocarbons and hydrogen and a heavy fraction 137 comprising C5+ hydrocarbons and predominantly comprises C5 olefins, monocyclic aromatics as well as unreacted pentanes from the feed stream. In certain embodiments, the first separator 135 is a two-phase splitter and separation of the alkylation effluent 134 is achieved by partial condensation. The light fraction 138 can be separated either be utilized as a fuel gas 152. Alternatively, hydrogen may be separated from the light fraction 130 and at least a portion of the remainder may form diluent stream 150 to be redirected and combined with feed stream 101 upstream from the first reactor 110, thereby serving as a reaction diluent for the feed stream 101 in the first reactor 110.

The heavy fraction 137 is conveyed to and received by a second separator 140 that may be a naphtha stabilizer. Second separator 140 is designed to separate the heavy fraction 137 into an aromatics fraction 142 that predominantly comprises monocyclic alkylated aromatics and a C5 recycle fraction 144 that predominantly comprises unreacted pentanes. In some embodiments, the second separator 140 is a naphtha stabilizer. The C5 recycle fraction 144 may optionally be recycled and combined with feed stream 101 upstream from the first reactor 110. Aromatics fraction 142 may optionally be conveyed to and received by a third separator 147 that separates benzene from the alkylated aromatics in the aromatics fraction to produce an alkylated aromatics product 150 that meets or exceeds government specifications for a liquid transportation fuel (or a blend component thereof) and a benzene stream 148 that is redirected to be combined with the second effluent 126 upstream from compressor 128.

Figure 2:
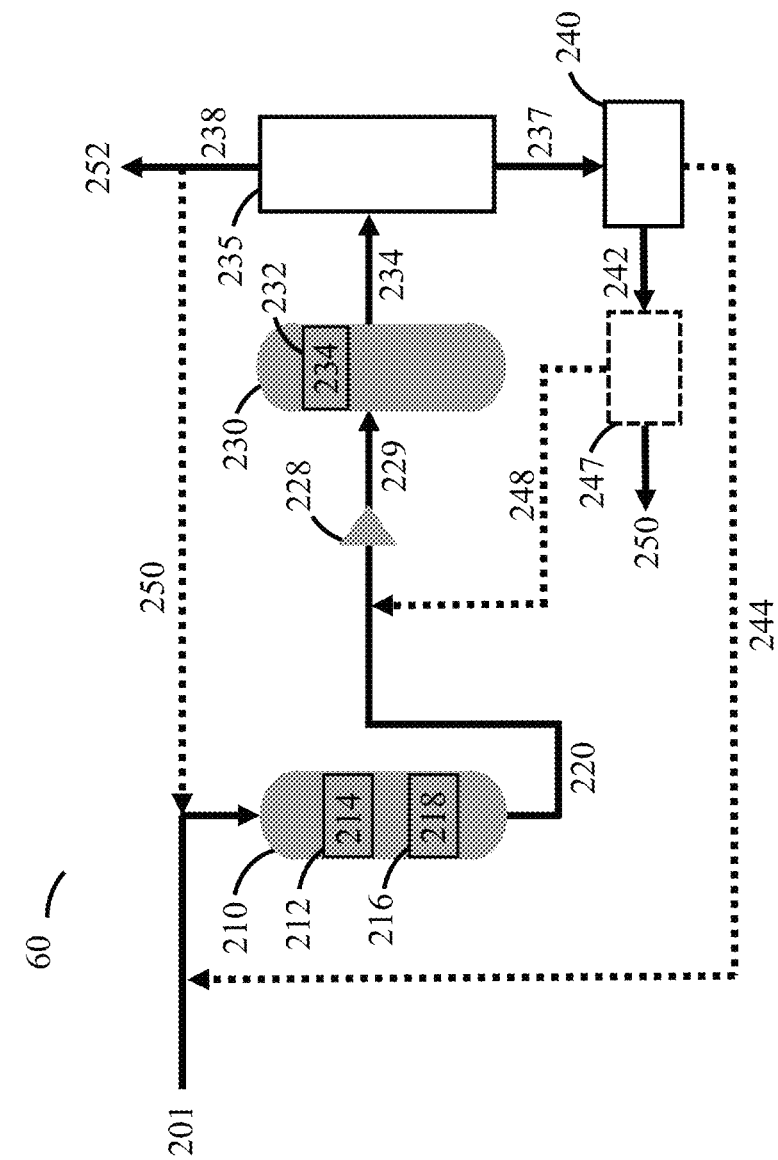
FIG. 2 is a flow diagram depicting a second embodiment of the inventive processes and systems.

A second embodiment of the inventive processes and systems is illustrated by the process flow-diagram of FIG. 2. A feed stream 201 that is enriched in pentanes is converted in a system 60. The feed stream 201 is received by a first reactor 210 comprising a first catalyst bed 212 that contains a first catalyst 214 and a second catalyst bed 216 comprising a second catalyst 218, with the two catalyst beds arranged in series within the first reactor 210. The first reactor 210 is operable to receive the feed stream 201 and to maintain a temperature and a pressure in the first catalyst bed 212 that facilitates catalytic conversion of the feed stream 201 by the first catalyst 214 to produce a first effluent (not depicted) comprising predominantly C2-C5 olefins, along with some monocyclic aromatics and alkanes (including unreacted pentanes).

The first effluent (not depicted) is next received by the second catalyst bed 216 containing a second catalyst 218. The first reactor 210 is operable to receive and maintain a temperature and a pressure in the second catalyst bed 216 that facilitates conversion of the first effluent by the second catalyst 218 to produce a second effluent 220 that is enriched in monocyclic aromatic content (on a molar basis relative to the first effluent) and additionally comprises olefins and some residual alkanes, including unreacted pentanes from the feed stream 201.

Speaking generally, embodiments that combine the first and second catalyst beds in the first reactor are designed such that the first reactor is operable to maintain the second catalyst bed at a temperature (typically measured at the inlet to the second catalyst bed) that is at least 25° F. lower, (optionally, at least 50° F. lower) than the temperature that is maintained in the first catalyst bed (typically measured at the inlet to the first catalyst bed).

Again referring to the embodiment diagram depicted in FIG. 2, The second effluent 220 is next conveyed to a compressor 228 that compresses the second effluent to a pressure that is higher than the pressure that is maintained in the first reactor 210 to produce a compressed second effluent 229 that is immediately conveyed to alkylation reactor 230 that comprises an alkylation catalyst bed 232 containing an alkylation catalyst 234. The alkylation reactor 230 is designed to maintain a temperature and a pressure that facilitates the contacting of the compressed second effluent 229 with the alkylation catalyst 234 at a temperature and a pressure that facilitate the alkylation of monocyclic aromatics in the compressed second effluent 229 with C1-C4 olefins present in the compressed second effluent to produce an alkylation effluent 234 that is enriched in mono-alkylated aromatics.

The alkylation effluent 234 is conveyed to and received by first separator 235, which is designed to separate hydrocarbons according to boiling point and thereby produce a light fraction 238 comprising C1-C4 hydrocarbons and hydrogen and a heavy fraction 237 comprising C5+ hydrocarbons and predominantly comprises C5 olefins, monocyclic aromatics as well as unreacted pentanes from the feed stream. In certain embodiments, the first separator 235 is a two-phase splitter and separation of the alkylation effluent 234 is achieved by partial condensation. The light fraction 238 can utilized as a fuel gas 252. Alternatively, hydrogen may be separated from the light fraction 238 and at least a portion of the remainder may form diluent stream 250 to be redirected and combined with feed stream 201 upstream from the first reactor 210, thereby serving as a reaction diluent for the feed stream 201 in the first reactor 210.

The heavy fraction 237 is conveyed to and received by a second separator 240 that may be a naphtha stabilizer. Second separator 240 is designed to separate the heavy fraction 237 into an aromatics fraction 242 that predominantly comprises monocyclic alkylated aromatics and a C5 recycle fraction 244 that predominantly comprises unreacted pentanes. In some embodiments, the second separator 240 is a naphtha stabilizer. The C5 recycle fraction 244 may optionally be recycled and combined with feed stream 201 upstream from the first reactor 210. Aromatics fraction 242 may optionally be conveyed to and received by a third separator 247 that may separate benzene from the alkylated aromatics in the aromatics fraction to produce an alkylated aromatics product 250 that meets or exceeds government specifications for a liquid transportation fuel (or a blend component thereof) and a benzene stream 248 that is redirected to be combined with the second effluent 226 upstream from compressor 228.

Speaking generally, the first catalyst comprises a zeolite that contacts alkanes present in the feed stream and facilitates C—H bond activation as an initial step toward producing products comprising olefins and aromatics. Speaking generally, the combination of first catalyst and conditions of temperature, pressure and space velocity in the first reaction zone (that are maintained by the first reactor) are selected to facilitate catalytic conversion of the feed stream by the first catalyst with high selectivity toward the production of C2-C5 olefins while minimizing selectivity toward the catalytic conversion of the feed stream to produce aromatics.

The second catalyst comprises a zeolite that contacts the first effluent and facilitates catalytic conversion of C2-C5 olefins present in the first effluent to produce aromatics and larger olefins (having a greater molecular weight) from the olefins in the first effluent. To a lesser extent, the second activation catalyst may also convert alkanes that remained unconverted in the first activation zone to produce olefins and aromatics. Speaking generally, the combination of second activation catalyst and conditions of temperature, pressure and space velocity in the second activation zone (that are maintained by the second activation reactor) are selective to facilitate C—H bond activation by the second catalyst as an initial step toward producing products comprising predominately monocyclic aromatics and a smaller amount of olefins. Restated, the second catalyst catalytically convert the first effluent by increased selectivity to production of aromatics while decreasing selectivity toward the production of olefins.

Each of the first and second catalysts comprise zeolites capable of activating hydrocarbons to produce olefins and/or aromatic hydrocarbons. In some embodiments the first activation catalyst is a zeolite that is selective toward the conversion of pentanes and/or isobutane to produce olefins via protonation of a C—H bond leading to a carbocation intermediate, and less selective for the production of monocyclic aromatics. In some embodiments, the second activation catalyst is a zeolite that is selective for the conversion of C2-C6 light olefins (and/or unreacted alkanes present in the feed stream) to monocyclic aromatics. In some embodiments, the first catalyst is compositionally-distinct from the second catalyst. In some embodiments, the first and second catalyst beds are fixed beds. Alternatively, the first and second catalyst beds may alternatively comprise a variety of known moving catalyst bed configurations, but an advantage of the present process is that it enables a longer catalytic life span due to the omission of dehydrogenating metals from the activation catalysts, enabling the use of a fixed bed configuration for the first and second catalysts.

Favored catalysts include supported or unsupported structured silica-aluminas that do not include additional impregnated metals. In some embodiments, ZSM-5 zeolite catalysts are utilized that are characterized by Si/Al ratios ranging from 12-80. In some embodiments, the activation catalyst utilized in the first catalyst bed is different from the activation catalyst utilized in the second catalyst bed. In some embodiments, the first catalyst is selective for the production of olefins (versus aromatics) when contacted with the feed stream and the second catalyst is selective for the production of aromatics (versus olefins) when contacted with the first effluent. In some embodiments, the first catalyst has a higher Bronsted Acidity than to the second catalyst. In some embodiments, the first catalyst has lower Lewis Acidity than to the second catalyst. In some embodiments, the first catalyst has a higher Bronsted acidity and a lower Lewis acidity than the second catalyst. In some embodiments, the first activation catalyst comprises a ZSM-5 catalyst with a Si/Al ratio in the range from 12-30, optionally in the range from 20-30. In some embodiments, the second activation catalyst comprises a ZSM-5 catalyst with a Si/Al ratio in the range from 31-80, optionally in the range from 35 to 50. In some embodiments, all catalysts utilized in the inventive process and system lack impregnated metals (other than Al) that promote dehydrogenation of alkanes, as this dehydrogenation reaction is equilibrium-limited and results in lower overall percent conversion of the light alkanes feed stream (less than 50 mole %). The lack of impregnated metals makes the zeolite catalyst utilized in the inventive processes and systems less expensive (i.e., decreased OPEX) and more resistant to deactivation by high sulfur containing feed stream (i.e., increased catalytic lifespan).

In the present inventive process a sufficient concentration of intermediate olefins is generated through the sequential, two-step catalytic activation such activation catalysts can be utilized that do not incorporate typical dehydrogenation promoting metals (such as platinum, zinc, molybdenum, or gallium) without significantly decreasing product yield. Known dehydrogenation-promoting metals are prone to poisoning by contaminants (including but not limited to, sulfur, nitrogen, arsenic and lead) that are often present in hydrocarbon feed streams derived from petroleum, so the ability of the process to proceed effectively in the absence of sensitive catalytic materials is highly advantageous to the present process. Further, dehydration is an equilibrium-limited reaction which limits yields production yields of favored olefins and aromatics. Utilizing activation catalysts without impregnated metals (other than Aluminum) allows increased yields of favored products without the upgrading reactions being equilibrium limited. This alleviates the need to recycle the feed one or more times to increase the yield of olefins and aromatics, as is done in many conventional processes.

The first catalyst bed contained within the first reactor is maintained at a temperature in the range from 500° C. to 650° C. (typically measured at the inlet of the first activation reactor). In some embodiments, the temperature in the first catalyst bed is maintained within the range from 525° C. to 625° C. In some embodiments, the temperature in the first catalyst bed is maintained within the range from 525° C. to 600° C. In some embodiments, the temperature in the first catalyst bed is maintained within the range from 550° C. to 600° C. In some embodiments, the temperature in the first catalyst bed is maintained within the range from 575° C. to 600° C.

The second catalyst bed contained within the second reactor is maintained at a temperature in the range from 475° C. to 625° C. (typically measured at the start of the catalyst bed) and at a temperature that is in the range from 25° C. to 75° C. cooler than the temperature that is maintained in the first catalyst bed. In some embodiments, the temperature in the second catalyst bed is maintained at a temperature in the range from 450° C. to 620° C. (typically measured at the inlet of the first catalyst bed) and at a temperature that is in the range from 30° C. to 70° C. cooler than the temperature that is maintained in the first catalyst bed. In some embodiments, the temperature in the second catalyst bed is maintained at a temperature in the range from 500° C. to 575° C. (typically measured at the inlet of the first catalyst bed) and at a temperature that is in the range from 40° C. to 60° C. cooler than the temperature that is maintained in the first catalyst bed. In some embodiments, the temperature in the second catalyst bed is maintained at a temperature that is 50° C. cooler than the temperature that is maintained in the first catalyst bed. In some embodiments, the temperature in the second catalyst bed is maintained within the range from 500° C. to 600° C. In some embodiments, the temperature in the second catalyst bed is maintained within the range from 500° C. to 575° C. In some embodiments, the temperature in the second catalyst bed is maintained within the range from 525° C. to 575° C.

The first catalyst bed contained within the first reactor is maintained at a pressure that favors the catalytic conversion of the feed stream to olefins (versus aromatics) by the first catalyst in the first catalytic bed. The conversion of light alkanes to light olefins (as opposed to aromatics) is favored at lower pressure. Thus, the first reactor maintains the first catalyst bed at a pressure in the range from 0 psig to 150 psig; Optionally, at a pressure in the range from 0 psig to 100 psig; Optionally, at a pressure in the range from 0 psig to 50 psig.

In some embodiments, the second reactor generally maintains the second catalyst bed at a pressure that is in the range between 0 psig and 500 psig. However, the conversion of light olefins and light alkanes (present in the first effluent) to aromatics is favored by higher pressure. Therefore, in some embodiments the second reactor maintains the second catalyst bed at a pressure in the range between 35 psig and 500 psig; optionally in the range between 50 psig and 300 psig; optionally, in the range between 50 psig and 200 psig; optionally, in the range between 50 psig and 150 psig.

In certain embodiments, the temperature maintained within the first catalyst bed (typically measured at the inlet of the first reactor) is lower than the temperature maintained in the second catalyst bed (typically measured at the inlet of the second activation reactor). Optionally, the first temperature may be at least 10° F. lower, at least 20° F. lower, at least 25° F. lower, at least 30° F. lower, at least 35° F. lower, at least 40° F. lower, at least 45° F. lower or at least 50° F. lower than the second temperature. Utilizing a lower temperature for the conversion of the first effluent in the second catalyst bed favors conversion of the first effluent to aromatics (versus cracking), thereby producing a second effluent with an approximate 1:1 molar ratio of C2-C4 light olefins to monocyclic aromatics. This makes the second effluent an excellent feed stream for a downstream alkylation process that is selective for the production of mono-alkylated aromatics having a Reid vapor pressure and octane rating that exceed specifications for a liquid transportation fuel blend stock. The final product of the process may be blended into liquid transportation fuel, separated and sold as one or more chemical products (i.e., Benzene, Xylene, Toluene, etc.) or utilized as feed stock for one or more additional process to produce value-added chemicals while minimizing the production of undesirable light hydrocarbons containing four or fewer carbons.

Speaking generally, the alkylation reactor is maintained at a feed inlet temperature and pressure suitable to facilitate the catalytic alkylation of aromatics present in the second effluent by the alkylation catalyst. The aromatics that are alkylated may be produced by aromatization that takes place in the first or second reactor, may be present in the feed stream for the process, or a combination of these possibilities. These aromatics are alkylated by olefins that are largely produced by the activation of alkanes in the first and, to a lesser extent, second reactors. Alkylation of aromatics by the alkylation catalyst produces larger aromatic hydrocarbons comprising at least seven carbon atoms that are preferably mono-alkylated and have a boiling point that is in the boiling point range of a liquid transportation fuel (e.g., gasoline or diesel). Typically, the alkylation effluent comprises an increased percentage of alkylated aromatic compounds comprising from seven to nine carbon atoms. Optionally, the larger hydrocarbons also are characterized by a lower Reid vapor pressure and an increased octane rating.

The alkylation reactor contains a bed of alkylation catalyst that may be in any known configuration including fixed bed, moving bed or ebulliated bed. The alkylation reactor is generally maintained at a pressure in a range from 0 psig to 800 psig, optionally in the range from 35 psig to 600 psig. The alkylation reactor is typically maintained at a temperature (measured within the alkylation reactor inlet or at the start of the alkylation catalyst bed) that is in the range from 150° C. to 350° C.; optionally between 200° C. to 350° C.; optionally, 250° C. to 350° C. Typically, flow thorough the alkylation reactor is maintained at a weighted hourly space velocity (WHSV) in the range from 0.5 $hr^{-1}$ to 10 $hr^{-1}$ on an olefin basis. Optionally, the WHSV is in the range from 0.5 $hr^{-1}$ to 6.0 $hr^{-1}$. While higher overall throughput is desirable, ideally the chosen WHSV allows for conversion of at least 85% of hydrocarbons present in the second effluent at the selected operating temperature and pressure.

In some embodiments, the catalytic conversion occurring in the alkylation reactor produces an alkylation effluent wherein the product comprises at least 30 wt. % (optionally, at least 40 wt %) of hydrocarbon molecules having a boiling-point that is within the boiling point range of a liquid transportation fuel. In some embodiments, the catalytic conversion occurring in the alkylation reactor produces an alkylation effluent wherein the product comprises less than 10 wt. % paraffins. In some embodiments, the catalytic conversion occurring in the alkylation reactor produces an alkylation effluent wherein the product comprises at least 50 wt. % aromatics; optionally at least 60 wt. % aromatics; optionally, at least 65 wt. % aromatics. In some embodiments, the catalytic conversion occurring in the alkylation reactor produces an alkylation effluent wherein the product comprises at least 40 wt. % mono-alkylated aromatics; optionally at least 50 wt. % mono-alkylated aromatics; optionally at least 60 wt. % mono-alkylated aromatics.

Speaking generally, the alkylation catalyst may comprise any catalyst characterized as either Brønsted or Lewis acidic. In some embodiments, the alkylation catalyst is supported on an acidic support which is well understood by to those having experience in the field. The Si/Al ratio of the alkylation catalyst may range from 12-80. In some embodiments, the catalyst may comprise a ZSM-5 catalyst with a Si/Al ratio of 23. A wide variety of catalysts have been found to promote aromatic alkylation including, but not limited to, aluminum chloride, phosphoric acid, sulfuric acid, hydrofluoric acid, silica, alumina, sulfated zirconia, zeolites (including, for example, ZSM-5, ZSM-3, ZSM-4, ZSM-18, ZSM-20, zeolite-beta, H-Y, MCM-22, MCM-36 and MCM-49).

Certain embodiments comprise mixing a diluent with the first fraction and/or the second fraction prior to contacting with the activation catalysts. The diluent may be added to the feed stream in a molar ratio ranging from 10:1 to 1:10 relative to the quantity of feed stream that is fed to the first activation zone. The diluent may be added at any point that is upstream from the first activation zone in the first activation reactor.

The diluent may comprise any substance that is less likely to be catalytically converted by one or more of the first activation catalyst and the second activation catalyst than the C2-C5 alkanes, olefins and aromatics present in the feed stream or first effluent at the conditions of temperature and pressure that are maintained within the first and second activation zones. This prevents the diluent from reacting with the first and second activation catalysts, which slows the overall catalytic conversion rate of compounds within the feed stream and/or first effluent by the activation catalysts. A large number of chemical compounds may serve as the diluent, the identity of which is fully within the grasp of one having experience in the art. In some embodiments the diluent comprises one or more light paraffins having from one to four carbon atoms, including C1-C4 light paraffins produced by the processes and systems described herein and recycled to be combined with the feed stream. In some embodiments the diluent may comprise any of methane, ethane, propane, butanes, benzene, toluene, xylenes, alkyl- or dialkyl-benzenes, naphthenes, C2-C5 olefins and combinations thereof.

The presence of diluent during catalytic activation (i.e., activation) provides several advantages. First, it effectively decreases the concentration of catalytically-convertible hydrocarbons in the feed stream within the first reactor, decreases the concentration of catalytically-convertible hydrocarbons within the second reactor, or both. This results in a small increase in the total conversion of pentanes (an increase of approximately 5-6 wt. %, typically) to produce olefins or aromatics within each activation reactor. However, it increases the selectivity toward the production of olefins in both the first and second effluent, while slightly decreasing the selectivity toward aromatics. Adjusting the ratio of diluent to feed stream changes the ratio of olefins to aromatics exiting the reactor, thereby providing a valuable point of operational control for downstream processes.

Addition of a diluent also advantageously favors the production of value-added olefins relative to C1-C4 light paraffins and decreases the dimerization rate of C5 hydrocarbons to form durene (1,2,4,5-tetramethylbenzene), a detrimental byproduct that can precipitate as a solid from liquid transportation fuels.

Typically, the composition of the feed stream, the first catalyst, the second catalyst, and the conditions maintained in the first reactor and the second reactor together produce a second effluent having a molar ratio of olefins to aromatics that is in the range from 0.5:1 to 1.5:1. In some embodiments, the composition of the feed stream, the first catalyst, the second catalyst, and the conditions maintained in the first reactor and the second reactor together produce a second effluent having a molar ratio of olefins to aromatics that is in the range from 0.8:1 to about 1.2:1 In some embodiments, the composition of the feed stream, the first catalyst, the second catalyst, and the conditions maintained in the first reactor and the second reactor together produce a second effluent having a molar ratio of olefins to aromatics that is in the range from 0.9:1 to about 1.1:1, which maximizes the conversion of aromatics and olefins in the second effluent to high octane (rating) mono-alkylated aromatics in the alkylation reactor, while minimizing selectivity to the production of di-alkylated and tri-alkylated aromatics. Mono-alkylated aromatics exhibit increased octane rating and decreased Reid vapor pressure properties and are favored gasoline blending components. In contrast, di-alkyl and tri-alkyl aromatics comprising more than nine carbon atoms are not well-suited for blending into gasoline and exhibit non-optimal cetane number for blending into diesel. The present inventive process maximizes conversion of the light alkanes feed stream to olefins and aromatics, while simultaneously producing a second effluent (that serves as feed for the alkylation reactor) that possesses an optimal ratio of olefins to aromatics to maximize production of high octane rating mono-alkylated aromatics that meet specifications for a gasoline blend stock.

EXAMPLES

The following examples are representative of one embodiment of the inventive processes and systems disclosed herein, and the scope of the invention is not intended to be limited to the embodiment specifically disclosed. Rather, the scope is intended to be as broad as is supported by the complete disclosure and the appending claims.

Example 1:

A 100 wt. % mixed pentanes feed stream (1:1 molar ratio of n-C5 to i-C5) was catalytically converted in two activation catalyst beds arranged in-series with the first catalyst bed maintained at a temperature of 575° C. and the second catalyst bed maintained at 500° C. with a WHSV=6.0 hr$^{-1}$. The activation catalyst for each of the first and second catalyst beds was ZSM-5. Results are time averaged for 16 hours and all reactions were carried out at 30 PSIG. Results were compared with a single temperature activation performed at either of the two temperatures utilized in the inventive two step activation process. Product distribution percentage reflects are normalized by subtracting unreacted feed stream.

TABLE 1

Two-step catalytic activation of pentanes compared to single-pass catalytic activation.

| Catalytic Process | Single-Pass Activation | Single-Pass Activation | In-Series Activation |
|---|---|---|---|
| Temperature | 575° C. | 500° C. | 575° C. then 500° C. |
| Conversion (mol %) | 53 | 42 | 73 |
| Recycle Molar Ratio (Recycle:Feed) | 4:1 | 4:1 | 4:1 |
| Product Selectivity (wt. %) | 76 | 78 | 72 |
| Lt. Olefin Selectivity (wt. %) | 65 | 44 | 32 |
| BTEX Aromatics Selectivity (wt. %) | 10 | 32 | 37 |
| Product Distribution (wt. %) | | | |
| Methane | 3 | 3 | 6 |
| Ethane | 8 | 6 | 10 |
| Ethene | 21 | 12 | 11 |
| Propanes | 11 | 5 | 10 |
| Propenes | 30 | 20 | 16 |
| Butanes | 4 | 6 | 4 |
| Butenes | 11 | 8 | 5 |
| Pentenes | 2 | 4 | 1 |
| C6+ Paraffins | 0 | 2 | 0 |
| Benzene | 3 | 7 | 9 |
| Toluene | 6 | 15 | 17 |
| Xylene | 1 | 9 | 10 |
| Ethyl-Benzene | 0 | 1 | 1 |

The results in Table 1 clearly demonstrate that when compared to a conventional one-step catalytic activation the two-step activation process decribed herein greatly decreased the quantity of C2-C4 olefins in the activation product, while simultaneously increasing the quantity of the monocylic aromatics benzene, toluene and xylene in the activation product.

Example 2:

A mixed pentanes enriched stream was catalytically converted in two activation reactors arranged in series, followed by an alkylation reactor. During activation each activation catalyst bed was maintained at a WHSV=6.0 hr$^{-1}$ a pressure of 30 psig and a temperature of 575° C. (first catalyst bed) and 500° C. (second catalyst bed) for the two activation reactors (in series configuration), The activation catalyst for each of the first and second catalyst beds was ZSM-5 while the aromatics alkylation catalyst was also a ZSM-5 material. The alkylation reactor was maintained at a temperature of 300° C. and a WHSV=1.3 hr$^{-1}$. Results were time averaged for 16 hours. Results were compared with a single temperature catalytic activation performed at either of the two temperatures utilized in the inventive two step activation process. Product distribution percentage reflects are normalized by subtracting unreacted feed stream. The product distribution was as shown in Table 2 (below):

TABLE 2

Product distribution of mixed pentanes feed stream following two step in-series activation followed by alkylation.

| | |
|---|---|
| Conversion (wt. %) | 71.1 |
| C1-C4 Paraffin Yield (wt. %) | 7.3 |
| Upgraded Product Yield (wt. %) | 51.9 |
| Coke Yield (wt. %) | 0.2 |
| C1-C4 Olefin Yield (wt. %) | 7.0 |
| Light Olefin Selectivity (%) | 9.8 |
| Liquid Product Yield (wt. %) | 44.9 |

TABLE 2-continued

Product distribution of mixed pentanes feed stream following
two step in-series activation followed by alkylation.

| | |
|---|---|
| Liquid Selectivity (%) | 63.2 |
| Alkylated Aromatics Yield? (wt. %) | 22.6 |
| Alkylated Aromatics Selectivity (%) | 27.0 |

TABLE 3

Product specifications for the non-stabilized liquid product
produced in Example 2.

| Component | Product (wt. %) |
|---|---|
| Paraffins | 9.1 |
| i-Paraffins | 8.5 |
| Aromatics | 68.1 |
| Mono-Aromatics | 63.9 |
| Olefins (wt. %) | 3.0 |
| RON (calculated) | 97.0 |
| MON (calculated) | 88.6 |
| Avg. Molecular Weight | 102.1 |
| Avg. Specific Gravity | 0.81 |
| Avg API @ 60° F. | 42.3 |
| RVP (psi) | 5.1 |
| Total Hydrogen | 10.9 |
| C/H ratio | 7.9 |
| Benzene Content (vol. %) | 4.8 |

Example 3:

The effect that a methane diluent has on catalytic activation and conversion of a simulated "natural gasoline" comprising a mixture of pentane isomers was next demonstrated. The feed stream was fed at a WHSV of 1.3 hr$^{-1}$ to a reactor containing an activation catalyst comprising a ⅛ extrudate consisting of 50 wt. % alumina binder and 50 wt. % ZSM-5 zeolite. The temperature of the reactor (at the inlet for the feed stream) was maintained at 600° C. and 20 psig (2.4 Bar) and results were time-averaged for 16.5 hr. For certain reactions, methane diluent was co-fed along with each feed stream at a methane:feed stream molar ratio of 2:1.

The reaction produced an effluent comprising light olefins, aromatics and light paraffins. Table 4 (below) shows the effect of the methane diluent on the total conversion of the 1:1 and 7:3 feed streams, respectively, as well as the selectivity of each conversion toward light olefins, aromatics, and byproduct C1-C4 fuel gas.

TABLE 4

Catalytic activation of a 1:1 i-C5:n-C5 feed stream in both the
absence and presence of methane diluent.

| Feed Stream +/− Diluent | Mixed Pentanes No Diluent | Mixed Pentanes CH$_4$ Diluent |
|---|---|---|
| Material Balance | 101% | 103% |
| Conversion | 92% | 80% |
| Fuel gas yield | 37% | 22% |
| Product Yield | 54% | 58% |
| Coke Yield | 0% | 0% |
| Lt. Olefin Yield | 34% | 44% |
| Lt. Olefin Selectivity | 37% | 55% |
| Aromatic Yield | 20% | 14% |
| Aromatic Selectivity | 21% | 17% |
| Fuel Gas Yield | 37% | 22% |
| Fuel Gas Selectivity | 41% | 27% |

The data in Table 5 indicate that adding an inert alkane diluent slightly decreased overall conversion rate, but significantly increased the yield and selectivity to light olefin production for the pentanes feed stream. Adding inert diluent also greatly diminished selectivity to the production of C1-C4 fuel gas. Meanwhile, only a small drop in selectivity to aromatics production was observed in the presence of diluent, which was offset by an equivalent increase in aromatics production. All of these results are advantageous to the process, particularly for embodiments where the second effluent is immediately conveyed to either an oligomerization or alkylation process. In certain embodiments that comprise an oligomerization process, diluent is added to the feed stream at a ratio that maximizes light olefin production, providing an advantageous feed stream for the oligomerization catalyst. In certain embodiments that comprise an aromatic alkylation process, diluent can be added to the feed stream or the first effluent at a ratio that helps adjust the molar ratio of produced olefins to aromatics to a value that is between 0.5:1 and 1.5:1 by mole, (optimally 1:1), thereby providing an advantageous feed for a downstream aromatic alkylation process.

Example 4

A 100 wt. % mixed pentanes feed stream (1:1 molar ratio of n-C5 to i-C5) was catalytically converted in two activation catalyst beds arranged in-series with the first catalyst bed maintained at a temperature of 575° C. and the second catalyst bed maintained at 500° C. with a WHSV=6.0 hr$^{-1}$. The activation catalyst for each of the first and second catalyst beds was ZSM-5. Results are time averaged for 16 hours and all reactions were carried out at 30 PSIG. Results were compared with a single temperature activation performed at either of the two temperatures utilized in the inventive two step activation process. Product distribution percentage reflects are normalized by subtracting unreacted feed stream.

TABLE 5

Two-step catalytic activation of isobutane compared to
single-pass catalytic activation.

| Catalytic Process | In Series Activation | In-Series Activation |
|---|---|---|
| Temperature | 575° C. then 525° C. | 600° C. then 550° C. |
| Conversion (mol %) | 73.5 | 92.7 |
| Recycle Molar Ratio (Recycle:Feed) | 4:1 | 4:1 |

TABLE 5-continued

Two-step catalytic activation of isobutane compared to single-pass catalytic activation.

| Catalytic Process | In Series Activation | In-Series Activation |
|---|---|---|
| Product Selectivity (wt. %) | 79.4 | 78.9 |
| Lt. Olefin Selectivity (wt. %) | 37.8 | 32.6 |
| BTEX Aromatics Selectivity (wt. %) | 37.3 | 43.2 |
| Methane | 8.3 | 9.5 |
| Ethane | 1.7 | 3.2 |
| Ethene | 6.7 | 9.2 |
| Propanes | 6.6 | 8.8 |
| Propenes | 11.9 | 12.7 |
| Butanes (unreacted feed stream) | 26.5 | 7.3 |
| Butenes | 8.4 | 8.0 |
| Pentanes | 1.4 | 0.6 |
| Pentenes | 0.9 | 0.6 |
| C6+ Paraffins | 1.3 | 1.7 |
| Benzene | 6.5 | 13.2 |
| Toluene | 14.3 | 18.5 |
| Xylene | 5.0 | 6.0 |
| Ethyl-Benzene | 0.6 | 0.6 |

The results in Table 5 clearly demonstrate that when compared to a conventional one-step catalytic activation for isobutane, the two-step activation process decribed herein greatly decreased the quantity of C2-C4 olefins in the activation product, while simultaneously increasing the quantity of the monocylic aromatics benzene, toluene and xylene in the activation product.

Definitions:

In the present disclosure, the term "conversion" is defined as any of the chemical reactions that occur during upgrading of hydrocarbons to liquid transportation fuels. Examples of such reactions include, but are not limited to: oligomerization, aromatization, dehydrogenation, alkylation, hydrogenation and cracking.

We claim:

1. A method for converting a feed stream comprising pentanes to produce a liquid transportation fuel, comprising:
   a. providing a hydrocarbon feed stream comprising at least 50 wt. % pentanes and less than 10 wt. % hydrocarbons that contain four or fewer carbon atoms;
   b. contacting the hydrocarbon feed stream with a first catalyst comprising a zeolite at conditions comprising a first temperature and a first pressure that facilitate conversion of at least a portion of the first fraction by the first catalyst to produce a first effluent comprising olefins containing from two to five carbon atoms, monocyclic aromatics and alkanes containing from two to five carbon atoms;
   c. contacting the first effluent with a second catalyst at conditions comprising a second temperature and second pressure that facilitates conversion of the first effluent by the second catalyst to produce a second effluent comprising monocyclic aromatics and olefins containing from two to five carbon atoms at a molar ratio that is in the range from 0.75 to 1.25, wherein the second catalyst has a distinct chemical composition from the first catalyst; wherein the second temperature is at least 25° C. lower than the first temperature;
   d. contacting the second effluent with an alkylation catalyst at a third temperature and a third pressure that facilitate alkylation of at least a portion of the aromatics in the second effluent with at least a portion of the olefins present in the second effluent by the alkylation catalyst to produce an alkylation effluent comprising an increased quantity of mono-alkylated aromatics containing eight or nine carbon atoms relative to the quantity of mono-alkylated aromatics containing eight or nine carbon atoms in the second effluent, wherein the alkylation effluent comprises at least 50 wt. % mono-alkylated aromatics containing from 7 to 9 carbon atoms;
   e. at least partially condensing the alkylation effluent to produce a heavy hydrocarbons fraction comprising hydrocarbons containing at least five carbon atoms and a light hydrocarbons fraction comprising hydrocarbons containing four or less carbon atoms;
   f. separating a C5 fraction comprising pentanes from the heavy hydrocarbon fraction to produce an aromatics product comprising mono-alkylated aromatics and residual benzene that meets specifications for a component of a liquid transportation fuel;
   g. redirecting the C5 fraction to be combined with the feed stream.

2. The method of claim 1, wherein the contacting of the first effluent with the second catalyst at conditions comprising a second temperature and second pressure facilitates conversion of the second fraction by the second catalyst to produce a second effluent comprising monocyclic aromatics and olefins containing from two to five carbon atoms at a molar ratio that is in the range from 0.9 to 1.1.

3. The method of claim 1, wherein the first catalyst and the second catalyst are zeolites that do not comprise metals other than aluminum.

4. The method of claim 1, wherein the hydrocarbon feed stream comprises less than 5 wt. % of hydrocarbons containing four or fewer carbon atoms.

5. The method of claim 1, wherein the hydrocarbon feed stream comprises at least 60 wt. % pentanes.

6. The method of claim 1, wherein first temperature is in the range from 500° C. to 650° C. and the first pressure is in the range from 0 psig to 150 psig.

7. The method of claim 1, wherein the second temperature is in the range from 475° C. to 625° C. and the second pressure is in the range from 0 psig to 500 psig.

8. The method of claim 1, wherein the third temperature is in the range from 150° C. to 350° C. and the third pressure is in the range from 35 psig to 600 psig.

9. The method of claim 1, wherein the second temperature is at least 25° C. lower than first temperature.

10. The method of claim 1, wherein the second pressure is at least 50 psi (3.45 Bar) higher than the first pressure.

11. The method of claim 1, further comprising adding a hydrocarbon diluent to the feed stream prior to the contacting of b) wherein the diluent is inert at the conditions of temperature and pressure that are maintained in the first catalyst bed.

12. The method of claim 11, wherein the diluent is obtained by separating C1-C4 hydrocarbons from the light fraction and redirecting the C1-C4 alkanes to be combined with the feed stream as the diluent.

13. A system for converting a feed stream comprising pentanes to produce a liquid transportation fuel or a component thereof, comprising:
   a. a first reactor comprising a first catalyst bed that contains a first catalyst comprising a zeolite, wherein the first reactor is operable to receive a hydrocarbon feed stream a hydrocarbon feed stream comprising at least 50 wt. % pentanes and less than 10 wt. % hydrocarbons that contain either from one to four or at least seven carbon atoms and to facilitate contact between the hydrocarbon feed stream and the first catalyst, wherein the first reactor is further operable to maintain the first catalyst bed at a first temperature and a first pressure that facilitates the catalytic conversion of the hydrocarbon feed stream by the first catalyst to produce a first effluent comprising olefins containing from two to five carbon atoms, monocyclic aromatics and unconverted alkanes containing from two to five carbon atoms;

b. a second reactor comprising a second catalyst bed that contains a second catalyst comprising a zeolite, wherein the second reactor is operable to receive the first effluent and to facilitate contact between the first effluent and the second catalyst, wherein the second reactor is further operable to maintain the second catalyst bed at a second temperature that is at least 25° C. lower than the first temperature and a pressure that is at least 50 psig (3.45 Bar) higher than the first pressure to facilitate the catalytic conversion of the first effluent by the second catalyst to produce a second effluent comprising monocyclic aromatics and olefins containing from two to five carbon atoms at a molar ratio that is in the range from 0.75 to 1.25, wherein the second catalyst has a distinct chemical composition from the first catalyst; wherein the second temperature is at least 25° C. lower than the first temperature;

c. a third reactor comprising a third reaction zone that contains an alkylation catalyst, wherein the third reactor is operable to receive the second effluent and facilitate contact between the second effluent and the alkylation catalyst in the third reaction zone, wherein the third reactor is operable to maintain the third reaction zone at a temperature and a pressure that facilitates alkylation of the monocyclic aromatics in the second effluent with the C2-C4 olefins from second effluent to produce an alkylation effluent comprising an increased quantity of mono-alkylated aromatics containing eight or nine carbon atoms relative to the quantity of mono-alkylated aromatics containing eight or nine carbon atoms in the second effluent;

d. a first separator operable to separate and partially condense the alkylation effluent to produce a heavy fraction and a light fraction, wherein the heavy fraction comprises monocyclic aromatics and unreacted alkanes containing at least five carbon atoms, wherein the light fraction comprises hydrogen and at least 80 wt. % olefins and alkanes containing four or fewer carbon atoms;

e. a second separator operable to separate a benzene stream from the heavy fraction to produce an aromatics product comprising mono-alkylated aromatics and residual benzene that meets specifications for a component of a liquid transportation fuel, wherien the system further comprises a first conduit operable to convey the benzene stream to be combined with the second effluent;

f. a third separator operable to separate hydrogen from the light fraction to produce a diluent stream comprising C1-C4 olefins and alkanes, wherein the system further comprises a second conduit operable to convey the recycle stream to be combined with the feed stream.

14. The system of claim 13, further comprising a compressor operable to compress the second effluent to produce a compressed second effluent that is at a higher pressure than the second effluent, wherein the alkylation reactor is operable to receive the compressed second effluent.

15. The system of claim 13, wherein the alkylation reactor is operable to receive a benzene stream in addition to the heavy hydrocarbons fraction and a first portion of the light hydrocarbons fraction.

16. The system of claim 13, wherein the first reactor is operable to maintain a first temperature in the first catalyst bed that is in the range from 500° C. to 650° C. and a pressure in the first catalyst bed that is in the range from 15 psig to 150 psig.

17. The system of claim 13, wherein the second reactor is operable to maintain the second temperature in the range from 475° C. to 625° C. and the second pressure in the range from 0 psig to 500 psig.

18. The system of claim 13, wherein the third reactor is operable to maintain the third temperature in the range from 150° C. to 350° C. and the third pressure in the range from 35 psig to 600 psig.

19. The system of claim 13, wherein the second reactor is operable to maintain the second catalyst bed at a temperature that is at least 25° C. lower than first temperature.

20. The system of claim 13, wherein the second reactor is operable to maintain the second pressure at a value that is at least 50 psi (3.45 Bar) higher than the first pressure.

* * * * *